United States Patent
Silverman et al.

(10) Patent No.: US 8,138,121 B2
(45) Date of Patent: Mar. 20, 2012

(54) USE OF PIPERONYL BUTOXIDE TO PROTECT PLANTS

(75) Inventors: Franklin Paul Silverman, Highland Park, IL (US); Peter D. Petracek, Grayslake, IL (US); Jennifer C. Kochan, Palatine, IL (US); Derek D. Woolard, Zion, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 422 days.

(21) Appl. No.: 12/011,809

(22) Filed: Jan. 30, 2008

(65) Prior Publication Data

US 2008/0254986 A1    Oct. 16, 2008

Related U.S. Application Data

(60) Provisional application No. 60/898,737, filed on Jan. 31, 2007.

(51) Int. Cl.
*A01N 25/00* (2006.01)
(52) U.S. Cl. .................................... 504/116.1
(58) Field of Classification Search ........................ None
See application file for complete search history.

(56) References Cited

U.S. PATENT DOCUMENTS 5,883,112 A * 3/1999 Pilato et al. .................. 514/404

OTHER PUBLICATIONS

Sansberro et al. Foliar Sprays with ABA promote growth of *Ilex paraguariensis* by alleviating diurnal water stress. Plant Growth Regulation 42: 105-111, 2004 Kluwer Academic Publishers.*
Krochko et al. (+)-ABSCISIAC Acid 8'-Hydroxylase is a Cytochrome P450 Monooxygenase. Plant Physiol.(1998) 118: 849-860.*
Enhancement of thiazopyr bioefficacy by inhibitors of monooxygenases. Rao et al. Pesticide Science. vol. 45, Issue 3, pp. 209-213. Nov. 1995.*
Ahmad et al., "Synergism of insecticides provides evidence of metabolic mechanisms of resistance in the obliquebanded leafroller *Choristoneura rosaceana (Lepidoptera: Tortricidae)*", Pest Management Science, 2004 vol. 60, pp. 465-473.
Kroehko et al "Abscisic acid hydroxylase is a cytochrome P450 monooxygenase", Plant Physiology, 1998 vol. 118, pp. 849-860.
English-Loeb, G.M. "Plant drought stress and outbreaks of spider mites: a field test", Ecology, 1990 vol. 71, pp. 1401-1411.
Fennell et al., "The induction of hepatic cytochrome P-450 in C57 BL/10 and DBA/2 mice by isosafrole and piperonyl butoxide. A comparative study with other inducing agents", Chem. Biol. Interactions, 31 (1980) pp. 189-201.
Ryu et al., "Piperonyl butoxide and acenaphthylene induce cytochrome P450 1A2 and 1B1 mRNA in aromatic hydrocarbon-responsive receptor knock-out mouse liver", Molecular Pharmacology, 50 (1996), pp. 443-446.
Phillips et al., "Effect of piperonyl butoxide on cell replication and xenobiotic metabolism in the livers of CD-1 mice and F344 rats". Fundamental and Applied Toxicology 38, (1997), pp. 64-74.

* cited by examiner

*Primary Examiner* — Annette Para
(74) *Attorney, Agent, or Firm* — Wood, Phillips, Katz, Clark & Mortimer

(57) ABSTRACT

The present invention is directed to the use of piperonyl butoxide, alone or with S-(+)-abscisic acid or its salts to minimize stress to plants.

12 Claims, No Drawings

USE OF PIPERONYL BUTOXIDE TO PROTECT PLANTS

TECHNICAL FIELD

The present invention relates to agricultural methods and compositions.

BACKGROUND OF THE INVENTION

S-(+)-abscisic acid (ABA) is a plant hormone that is found in all photosynthetic organisms (Arteca, R., 1996,*Plant Growth Substances: Principles and Applications*. New York: Chapman & Hall). ABA is involved in many major events of plant growth and development including dormancy, germination, bud break, flowering, fruit set, general growth and development, stress tolerance, ripening, abscission, and senescence. One of the roles of ABA is the regulation of water relations in plants through the control of stomata opening and closure. Based on its effects on stress reduction, ABA is being developed for use on ornamental and crop plants.

The rapid metabolism and loss of ABA may be a limiting factor for its development as a commercial plant growth regulator. Therefore, it is an object of the present invention to increase the effectiveness of ABA in the protection of plants from stress.

It is an object of this invention to increase the resistance of plants to stress with the application of piperonyl butoxide (PBO).

It is an object of this invention to increase the resistance of plants to stress with the application of combinations of ABA and PBO.

It is a further object of the present invention to protect plants from drought stress.

SUMMARY OF THE INVENTION

The present invention is directed to a method of protecting plants from stress by applying an effective amount of PBO to the foliage of plants.

The present invention is also directed to a method of increasing the drought-protection activity of ABA by applying an effective amount of ABA or its salts and PBO to the foliage of plants.

The present invention is also directed to a method of lengthening the time of ABA effectiveness by applying, an effective amount of ABA or its salts and PBO to the foliage of plants.

The present invention is also directed to a method of lengthening the time of ABA effectiveness by applying ABA or its salts to the potting soil and an effective amount of PBO to the foliage of the treated plant.

The present invention is further directed to an agricultural composition that comprises ABA or its salts and PBO.

DETAILED DESCRIPTION OF THE INVENTION

S-(+)-abscisic acid is a naturally occurring plant hormone which acts primarily to inhibit growth, maintain dormancy of buds, promote fruit maturation or coloration, activate the defense response against pathogens, induce senescence, and help the plant tolerate stressful conditions. See Arteca, R. (1996), *Plant Growth Substances: Principles and Applications*. New York: Chapman & Hall; Mauseth, J. D. (1991), *Botany: An Introduction to Plant Biology*. Philadelphia: Saunders. pp. 348-415; Raven, P. H., Evert, R. F., and Eichhorn, S. E. (1992), *Biology of Plants*. New York: Worth. pp. 545-572.

S-(+)-abscisic acid owes its name to early studies with this plant growth regulator that showed abscission of leaves. The chemistry and physiology of abscisic acid and its analogs is described by Milborrow, Ann. Rev. Plant Physiol. 1974, 25, 259-307.

The composition of the present invention may contain from about 0.01 to about 20 wt % ABA or its salts and from about 0.01 to about 50 wt. % PBO.

The applied concentration of ABA or its salts can vary widely and is generally in the range of about 0.1 to about 5000 ppm, preferably from about 10 to about 1000 ppm and the concentration of PBO is generally in the range of about 0.1 to about 5000 ppm, preferably from about 10 to about 2000 ppm.

As used herein, the term "salt" refers to the water soluble salts of ABA or ABA analogs or derivatives, as appropriate. Representative such salts include inorganic salts such as the ammonium, lithium, sodium, potassium, calcium and magnesium salts and organic amine salts such as the triethanolamine, dimethylethanolamine and ethanolamine salts.

As used herein the term "stress" refers to any environmental condition that could adversely effect a plant, as for example, drought, heat, cold, excess water or flooding.

The following procedures are utilized in the illustrative examples that follow.

Procedures

Plant Materials:

Cotton was planted and grown at 25° C. under a 16:8 photoperiod for 14 days. After two weeks, plants were moved to the greenhouse (25±2° C., 16:8 photoperiod) for an additional three weeks before treatment.

Ornamental Plants were purchased from local greenhouse retail outlets and allowed to equilibrate to greenhouse conditions for a minimum of 48 hours before experiments were performed.

Transpiration Measurements:

Leaf transpiration rate was measured at times 5, 24, 48, 72 or 96 hours after treatment using a LI-1600 Steady State Porometer (LI-Cor, Lincoln, Nebr.). Transpiration rate of each treatment was calculated as the percentage of that of control at each day to eliminate day-to-day variation caused by changes of environmental condition such as light intensity and temperature.

Wilt Index:

To quantify resistance of plants to wilting, a wilt index was developed. The wilt index uses numerical values of 1-4 (1=no wilt, 4=completely wilted and loss of turgor) to express wilt status. A wilt index was determined for each individual plant assessed daily. When the wilt index was equal to or exceeded 2.5, the plant was considered not salable, and the last day prior to that was considered its last marketable day

EXAMPLE 1

In cotton, ABA, PBO and the combination were applied to evaluate the effect on stomatol conductance. A decrease in stomatal aperture, reflected in the conductance measures, is an immediate and direct effect of applied ABA (Finkelstein and Rock, 2002).

In Table 1, plants were drenched treated with 10 percent of their volume (20 mL/pot), and stomatal conductance was measured at the times indicated.

TABLE 1

Effect of drenches with abscisic acid (ABA) and piperonyl butoxide (PBO) on stomatal conductance of cotton. plants.*

| Treatment | Hours after drench application | | | | | |
|---|---|---|---|---|---|---|
| | 0 | 5 | 24 | 48 | 72 | 96 |
| Control | 100.0 | 100.0 | 100.0 | 100.0 | 100.0 | 100.0 |
| ABA 50 ppm | 100.3 | 56.0 | 77.5 | 85.8 | 83.9 | 104.3 |
| PBO 50 ppm | 100.8 | 84.0 | 95.1 | 97.7 | 91.6 | 101.5 |
| PBO 500 ppm | 100.4 | 86.8 | 89.8 | 96.9 | 100.2 | 93.1 |
| ABA 50 + PBO 50 | 101.9 | 41.1 | 77.2 | 92.3 | 81.3 | 101.2 |
| ABA 50 + PBO 500 | 104.7 | 68.4 | 89.0 | 87.7 | 90.1 | 102.1 |

*Percent Conductance: All data have been normalized so control at each time point is 100% conductance.

Drench treatments with 50 ppm ABA were only effective at reducing stomatal conductance by 44% or 22.5% at 5 or 24 hours post drench treatments, respectively. Only at 24 hours was the effect of ABA drench significantly different than the control. Treatments with PBO were not significantly different from the control, at any time point, although numeric decreases in stomatal conductance were observed. Combinations with ABA did not consistently increase ABA activity, and did not statistically differ from the ABA only treatment at any time point.

In order to determine if spray treatments would be more effective, ABA and PBO were spray applied to cotton, as is shown in Table 2.

TABLE 2

Effect of sprays with ABA and PBO on stomatal conductance of cotton. plants.*

| Treatment | Hours after spray application | | | | | |
|---|---|---|---|---|---|---|
| | 0 | 5 | 24 | 48 | 72 | 96 |
| Control | 100.0 | 100.0 | 100.0 | 100.0 | 100.0 | 100.0 |
| ABA 50 ppm | 101.1 | 41.1 | 86.2 | 91.9 | 102.0 | 100.6 |
| PBO 50 ppm | 101.8 | 89.6 | 100.7 | 100.2 | 90.2 | 96.2 |
| PBO 500 ppm | 103.0 | 67.2 | 68.5 | 81.5 | 84.6 | 95.2 |
| ABA 50 + PBO 50 | 103.8 | 76.9 | 94.7 | 98.9 | 100.7 | 97.1 |
| ABA 50 + PBO 500 | 104.6 | 14.1 | 35.9 | 65.8 | 89.7 | 91.1 |

*Percent Conductance: All data have been normalized so control at each time point is 100% conductance.

In contrast to the experiment shown in Table 1, PBO effectively reduced stomatal conductance in a dose-dependent manner when spray applied. ABA sprays were faster acting than drench treatments, with a significant (58.9%) decrease in stomatal conductance observed at 5 hours after spray application. The addition of PBO at 500 ppm to ABA sprays significantly increased the effectiveness of the sprays as compared to ABA alone. At 5 hours, the addition of PBO increased the effect of ABA on stomatal conductance by 27%. While ABA did not significantly affect stomatal conductance at 24 or 48 hours after spraying, the addition of 500 ppm PBO significantly increased ABA effectiveness at both times. PBO at 500 ppm alone was less effective at reducing stomal conductance than the combination with ABA.

EXAMPLE 2

In the ornamental plant Impatiens, spray applications were made to evaluate the effects of ABA, PBO or the combination to increase the number of days until the plants wilted. Using a wilt index of 1-4 (1=no wilt, 4=completely wilted and loss of turgor), plants were evaluated following spray application.

TABLE 3

Effect of ABA and PBO sprays on wilt index* of Impatiens plants

| Treatment | Days after Spray Application | | | | |
|---|---|---|---|---|---|
| | 0 | 4 | 5 | 6 | 7 |
| Water + Tween 20, 0.05% | 1 | 1.27 | 1.88 | 2.63 | 3.08 |
| ABA 200 ppm + Tween 20 0.05% | 1 | 1.00 | 1.27 | 1.66 | 2.31 |
| PBO 1000 ppm + Tween 20 0.05% | 1 | 1.13 | 1.34 | 1.83 | 2.25 |
| ABA200 + PBO 1000 + Tween 20 0.05% | 1 | 1.08 | 1.14 | 1.14 | 1.53 |

*Wilt Index: 1 = no wilt; 4 = plants wilted, complete loss of turgor.

As expected, ABA application slowed and reduced incidence of wilting. PBO also resulted in a reduction of wilt intensity and slowed wilt incidence. The combination of ABA and PBO was superior at controlling plant wilting than either agent alone.

The slowing of wilt incidence by the treatments allowed for a comparison of marketability after treatment. When the wilt incidence was less than 2.5, the treated plants were considered saleable. The duration of salability was determined for individual plants and the values averaged (Table 4).

TABLE 4

Effect of ABA and PBO sprays on marketability of Impatiens plants

| Treatment | Days Marketable (Wilt index less than 2.5) |
|---|---|
| Water + Tween 20, 0.05% | 5.8 |
| ABA 200 ppm + Tween 20 0.05% | 7.5 |
| PBO 1000 ppm + Tween 20 0.05% | 6.6 |
| ABA 200 ppm + PBO 1000 ppm + Tween 20 0.05% | 7.9 |

*Days marketable was determined for each individual plant assessed daily. When the wilt index was equal to or exceeded 2.5, the plant was considered not salable, and the last day prior to that was considered its last marketable day.

Similar to the study shown in Table 3, ABA application significantly slowed plant wilting, providing an almost two day increase in shelf life without watering. PBO application resulted in a significant benefit in wilt control over the control spray treatments, although not as good as observed with ABA in this study. The combination of ABA and PBO was superior to either treatment alone, but was not significantly different from ABA using an ANOVA and p=0.05. A student's t test showed the difference between the treatments at p=0.06, indicating that the two means are different, and a difference would be observed in greater than 9 of 10 tests.

EXAMPLE 3

To better determine the effectiveness of PBO on ABA effectiveness, a spatial separation in application methodology was used. That is, water or ABA were drench applied at 10% of the pot volume, followed by a spray application to the foliage of Tween 20 (0.05%) in water, either alone, or in combination with 1000 ppm PBO.

TABLE 5

Effect of ABA and PBO treatments on marketability of *Impatiens* plants

| Drench Treatment | Spray Treatment | Days Marketable (Wilt index less than 2.5) |
|---|---|---|
| Water | Tween 20 0.05% | 5.56 |
| ABA 200 ppm | Tween 20 0.05% | 7.69 |
| Water | PBO 1000 ppm + Tween 20 0.05% | 6.69 |
| ABA 200 ppm | PBO 1000 ppm + Tween 20 0.05% | 8.72 |

*Days marketable was determined for each individual plant assessed daily. When the wilt index was equal to or exceeded 2.5, the plant was considered not salable, and the last day prior to that was considered its last marketable day.

The results of the study in Table 5 demonstrate that ABA and PBO applications are additive for increasing marketable shelf life, even when the applications are made to separate plant tissues.

In Table 6, the rate of ABA in the drench application is varied in order to determine the effect of PBO sprays on ABA rate.

TABLE 6

Effect of ABA and PBO treatments on marketability of *Impatiens* plants

| Drench Treatment | Spray Treatment | Days Marketable (Wilt index less than 2.5) |
|---|---|---|
| Water | Tween 20, 0.05% | 5.3 |
| ABA 50 ppm | Tween 20, 0.05% | 6.5 |
| ABA 200 ppm | Tween 20, 0.05% | 8.1 |
| Water | PBO 1000 ppm + Tween 20, 0.05% | 6.5 |
| ABA 50 ppm | PBO 1000 ppm + Tween 20, 0.05% | 8.6 |
| ABA 200 ppm | PBO 1000 ppm + Tween 20, 0.05% | 9.6 |

*Days marketable was determined for each individual plant assessed daily. When the wilt index was equal to or exceeded 2.5, the plant was considered not salable, and the last day prior to that was considered its last marketable day.

As shown in the study in Table 6, PBO was additive to ABA application, irrespective of ABA rate. PBO sprays alone were equal to 50 ppm ABA in increasing marketable life of Impatiens, while the combination of PBO with 50 ppm ABA was statistically equal to a 200 ppm ABA drench. The effect of PBO on ABA drenches for increasing the market life of Impatiens is additive.

EXAMPLE 4

To determine if the combination of ABA and PBO is effective at increasing marketable life of other ornamental plants, Viola plants (Violet) were used. All applications were made by spray to fully hydrated plants. Spray solutions were applied as soon as possible after mixing. All spray applications contained Tween 20 at 0.05% (v/v).

TABLE 7

Effect of ABA and PBO treatments on marketability of *Viola* (Violet)

| Spray Treatment | Days Marketable (Wilt index less than 2.5)* |
|---|---|
| Water + Tween 20, 0.05% | 5.3 |
| PBO 1000 ppm + Tween 20, 0.05% | 5.9 |
| ABA 100 ppm + Tween 20, 0.05% | 8.0 |
| ABA 100 ppm + PBO 1000 ppm + Tween 20, 0.05% | 8.4 |

*Days marketable was determined for each individual plant assessed daily. When the wilt index was equal to or exceeded 2.5, the plant was considered not salable, and the last day prior to that was considered its last marketable day.

Although PBO and ABA were separately able to significantly increase the marketable life of Viola, the combination was not significantly superior to ABA alone. This finding demonstrates the utility of PBO alone as an anti-wilting compound on Violets. Moreover, the addition of PBO to the ABA spray solution increased the marketable life by nearly half a day.

EXAMPLE 5

To determine if the ABA, PBO, or the combination of ABA and PBO is effective at increasing marketable life of other ornamental plants, Pansy plants were used. All applications were made by spray to fully hydrated plants. Solutions were applied as soon as possible after mixing. All spray applications contained Tween 20 at 0.05% (v/v). Plants were held in a greenhouse without further irrigation.

TABLE 8

Effect of ABA and PBO treatments on marketability of Pansy

| Spray Treatment | Days Marketable (Wilt index less than 2.5)* |
|---|---|
| Water + Tween 20, 0.05% | 4.4 |
| ABA 7.5 mg + Tween 20, 0.05% | 7.6 |
| PBO 1.5 mg + Tween 20, 0.05% | 5.8 |
| ABA 7.5 mg + PBO 1.5 mg + Tween 20, 0.05% | 7.0 |

*Days marketable was determined for each individual plant assessed daily. When the wilt index was equal to or exceeded 2.5, the plant was considered not salable, and the last day prior to that was considered its last marketable day.

Although PBO and ABA were separately able to significantly increase the marketable life of Pansy, the combination was not significantly superior to ABA alone. This finding demonstrates the utility of PBO alone as an anti-wilt compound on Pansy.

The invention claimed is:

1. A method of decreasing effects on plants from drought, chilling, flooding or heat stress comprising applying from about 500 ppm to about 2000 ppm of piperonyl butoxide and an effective amount of abscisic acid or salts thereof to the foliage of plants that are susceptible to drought, chilling, flooding or heat stress.

2. A method of increasing the drought mitigating activity of S-(+)-abscisic acid comprising applying from about 500 ppm to about 2000 ppm of piperonyl butoxide and an effective amount of S-(+)-abscisic acid or salts thereof to the foliage of plants that are susceptible to drought stress.

3. A method of lengthening the time of the effectiveness of S-(+)-abscisic acid in treating plants comprising applying an effective amount of S-(+)-abscisic acid or its salts to the foliage or potting soil of a plant in need of treatment and from about 500 ppm to about 2000 ppm of piperonyl butoxide to the foliage of said plant.

4. An agricultural composition for decreasing effects on plants from drought, chilling, flooding, or heat stress; comprising and effective amount of S-(+)-abscisic acid or its salts and from about 500 ppm to about 2000 ppm of piperonyl butoxide.

5. The method of claim 1 wherein the plants are cotton.

6. The method of claim 2 wherein the plants are cotton.

7. The method of claim 1 wherein the plants are impatiens.

8. The method of claim 2 wherein the plants are impatiens.

9. The method of claim 1 comprising application of about 500 ppm piperonyl butoxide.

10. The method of claim 2 comprising application of about 500 ppm piperonyl butoxide.

11. The method of claim 1 comprising application of about 1000 ppm piperonyl butoxide.

12. The method of claim 2 comprising application of about 1000 ppm piperonyl butoxide.

\* \* \* \* \*